United States Patent
Tan et al.

(10) Patent No.: US 10,378,426 B2
(45) Date of Patent: Aug. 13, 2019

(54) USEFUL LIFE PREDICTION SYSTEM FOR COOLING COMPONENTS

(71) Applicant: Caterpillar Inc., Peoria, IL (US)

(72) Inventors: Dongming Tan, Dunlap, IL (US); Doug A. Long, Washington, IL (US); Neil Terry, Edelstein, IL (US); Anthony L. Deluca, Germantown Hills, IL (US); Jianlong Xu, Mossville, IL (US); Rohit K. Paramatmuni, Peoria, IL (US); Joseph L. Kennedy, Peoria, IL (US); Michael J. Campagna, Chillicothe, IL (US)

(73) Assignee: Caterpillar Inc., Deerfield, IL (US)

( * ) Notice: Subject to any disclaimer, the term of this patent is extended or adjusted under 35 U.S.C. 154(b) by 284 days.

(21) Appl. No.: 15/381,904

(22) Filed: Dec. 16, 2016

(65) Prior Publication Data
US 2018/0171861 A1   Jun. 21, 2018

(51) Int. Cl.
*G07C 5/00* (2006.01)
*F02M 26/49* (2016.01)
(Continued)

(52) U.S. Cl.
CPC ............. *F01P 11/14* (2013.01); *F02M 26/49* (2016.02); *G07C 5/008* (2013.01); *F01P 11/16* (2013.01);
(Continued)

(58) Field of Classification Search
CPC ........ F01P 11/14; F01P 2023/08; F01P 11/16; F01P 2025/13; F01P 2025/46;
(Continued)

(56) References Cited

U.S. PATENT DOCUMENTS 6,260,998 B1   7/2001   Garfinkel et al.
6,301,970 B1   10/2001  Biggs et al.
(Continued)

FOREIGN PATENT DOCUMENTS

CN    103698222 A    4/2014
WO    WO 2015/135547 A1    9/2015

*Primary Examiner* — Stephen Holwerda
(74) *Attorney, Agent, or Firm* — Leydig, Voit & Mayer, Ltd.

(57) ABSTRACT

A system for determining a remaining useful life of a cooling component operatively connected to a prime mover. A controller performs a thermal strain analysis that includes determining the power output of the prime mover based upon sensor signals, determining a temperature output of the prime mover based upon the power output, determining a temperature at each of the plurality of analysis locations based upon the temperature output, determining a temperature difference based upon the temperature at each respective one of the plurality of analysis locations, and determining a thermal strain based upon the temperature difference. The controller repeats the thermal strain analysis at time intervals over a period of time, determines an accumulated damage for the cooling component based upon the thermal strain from each thermal strain analysis, and determines a remaining useful life of the cooling component based upon the material characteristics and the accumulated damage.

20 Claims, 5 Drawing Sheets

(51) Int. Cl.
*F01P 11/14* (2006.01)
*G01N 25/72* (2006.01)
*F01P 11/16* (2006.01)
*F02M 26/48* (2016.01)

(52) U.S. Cl.
CPC ....... *F01P 2023/08* (2013.01); *F01P 2025/13* (2013.01); *F01P 2025/46* (2013.01); *F01P 2025/50* (2013.01); *F01P 2025/62* (2013.01); *F01P 2025/64* (2013.01); *F01P 2031/20* (2013.01); *F01P 2060/02* (2013.01); *F01P 2060/04* (2013.01); *F02M 26/48* (2016.02); *G01N 25/72* (2013.01)

(58) Field of Classification Search
CPC ............... F01P 2025/50; F01P 2025/62; F01P 2025/64; F01P 2031/20; F01P 2060/02; F01P 2060/04; G01M 15/14; G01M 13/021; G07C 5/008; G07C 5/085; G01N 25/72; G08C 15/06; E02F 9/267; E02F 9/205; E02F 9/2242; E02F 9/2292; E02F 9/2296; E02F 9/26; G06Q 10/06; G06Q 50/30; Y04S 10/54; F02C 9/00; G06F 7/00; F05D 2260/80; F05D 2260/81; F02M 26/49; F02M 26/48
See application file for complete search history.

(56) References Cited

U.S. PATENT DOCUMENTS

| | | | |
|---|---|---|---|
| 6,349,252 B1* | 2/2002 | Imanishi | G08C 15/06 701/32.7 |
| 7,878,233 B2 | 2/2011 | Bates et al. | |
| 8,116,990 B2 | 2/2012 | Koul | |
| 9,018,782 B2 | 4/2015 | Couchman et al. | |
| 2004/0260512 A1* | 12/2004 | Olsson | G01M 13/021 702/182 |
| 2006/0212203 A1* | 9/2006 | Furuno | E02F 9/205 701/50 |
| 2014/0163838 A1* | 6/2014 | Moeckly | F02C 9/00 701/100 |
| 2014/0336954 A1 | 11/2014 | Bruyneel et al. | |
| 2015/0081121 A1 | 3/2015 | Morgan et al. | |

* cited by examiner

USEFUL LIFE PREDICTION SYSTEM FOR COOLING COMPONENTS

TECHNICAL FIELD

This disclosure relates generally to a useful life prediction system and, more particularly, to a system and method for evaluating prime mover operation and predicting the remaining useful life of cooling components associated with the prime mover and generating alerts or notifications based upon the remaining useful life.

BACKGROUND

Machines are used to perform various operations in different industries, such as construction, mining, transportation, and the like. Such machines may include an engine and one or more cooling components for cooling fluids and other aspects of the machine.

Operation of the machines, and the resulting generation of heat, causes temperature differences along and within the cooling components. The temperature differences along and within the cooling components cause thermal stress on the components. Over time, damage to the cooling components as a result of the thermal stress will accumulate and ultimately may result in a failure of the cooling components. Such failure may result in significant and unexpected machine downtime.

The useful life of a component subjected to stresses caused by pressure or acceleration may often track or correspond to the pressure or acceleration, respectively, to which the component is subjected. However, the useful life of a component subjected to thermal stresses is less likely to track or correspond to the temperature to which the component is exposed. In addition, determining the temperature along or within a component is often substantially more difficult than determining the pressure or acceleration to which the component is subjected.

U.S. Pat. No. 8,116,990 discloses a prognostics system for use with a turbine engine that continuously monitors the engine operating parameters and engine operating environment. The system further performs usage and operating environment based crack nucleation, crack propagation, distortion, corrosion or erosion analysis for life consumption and residual life prediction of multiple structural components of the turbine engine. Still further, the system predicts intrinsic and extrinsic states of damage in the structural components before the development of discernible faults or damage using standard data acquired from engine monitoring interfaces.

The foregoing background discussion is intended solely to aid the reader. It is not intended to limit the innovations described herein, nor to limit or expand the prior art discussed. Thus, the foregoing discussion should not be taken to indicate that any particular element of a prior system is unsuitable for use with the innovations described herein, nor is it intended to indicate that any element is essential in implementing the innovations described herein. The implementations and application of the innovations described herein are defined by the appended claims.

SUMMARY

In one aspect, a system for determining a remaining useful life of a cooling component operatively connected to a prime mover includes a power output sensor and a controller. The power output sensor is associated with the prime mover and is configured to generate sensor signals indicative of a power output of the prime mover. The controller is configured to store material characteristics of the cooling component, store a plurality of spaced apart locations of the cooling component that define a plurality of analysis locations, and receive sensor signals from the power output sensor. The controller is further configured to perform a thermal strain analysis that includes determining the power output of the prime mover based upon the sensor signals, determining a temperature output of the prime mover based upon the power output, determining a temperature at each of the plurality of analysis locations based upon the temperature output, determining a temperature difference between at least some of the plurality of analysis locations and another of the plurality of analysis locations based upon the temperature at each respective one of the plurality of analysis locations, and determining a thermal strain for each of the at least some of the plurality of analysis locations based upon the temperature difference. The controller is configured to repeat the thermal strain analysis at predetermined time intervals over a predetermined period of time, determine an accumulated damage for the cooling component based upon the thermal strain from each thermal strain analysis, and determine a remaining useful life of the cooling component based upon the material characteristics and the accumulated damage.

In another aspect, a controller-implemented method for determining a remaining useful life of a cooling component operatively connected to a prime mover includes storing material characteristics of the cooling component, storing a plurality of spaced apart locations of the cooling component that define a plurality of analysis locations, and receiving sensor signals from a power output sensor indicative of a power output of the prime mover. The method further includes performing a thermal strain analysis including determining the power output of the prime mover based upon the sensor signals, determining a temperature output of the prime mover based upon the power output, determining a temperature at each of the plurality of analysis locations based upon the temperature output, determining a temperature difference between at least some of the plurality of analysis locations and another of the plurality of analysis locations based upon the temperature at each respective one of the plurality of analysis locations, and determining a thermal strain for each of the at least some of the plurality of analysis locations based upon the temperature difference. The method includes repeating the thermal strain analysis at predetermined time intervals over a predetermined period of time, determining an accumulated damage for the cooling component based upon the thermal strain from each thermal strain analysis, and determining a remaining useful life of the cooling component based upon the material characteristics and the accumulated damage.

In still another aspect, a machine includes a prime mover, a cooling component operatively connected to the prime mover, power output sensor and a controller. The power output sensor is associated with the prime mover and is configured to generate sensor signals indicative of a power output of the prime mover. The controller is configured to store material characteristics of the cooling component, store a plurality of spaced apart locations of the cooling component that define a plurality of analysis locations, and receive sensor signals from the power output sensor. The controller is further configured to perform a thermal strain analysis that includes determining the power output of the prime mover based upon the sensor signals, determining a temperature output of the prime mover based upon the power output, determining a temperature at each of the plurality of analysis locations based upon the temperature output, determining a temperature difference between at least some of the plurality of analysis locations and another of the plurality of analysis locations based upon the temperature at each respective one of the plurality of analysis locations, and determining a thermal strain for each of the at least some of the plurality of analysis locations based upon the temperature difference. The controller is configured to repeat the thermal strain analysis at predetermined time intervals over a predetermined period of time, determine an accumulated damage for the cooling component based upon the thermal strain from each thermal strain analysis, and determine a remaining useful life of the cooling component based upon the material characteristics and the accumulated damage.

DETAILED DESCRIPTION

Figure 1:
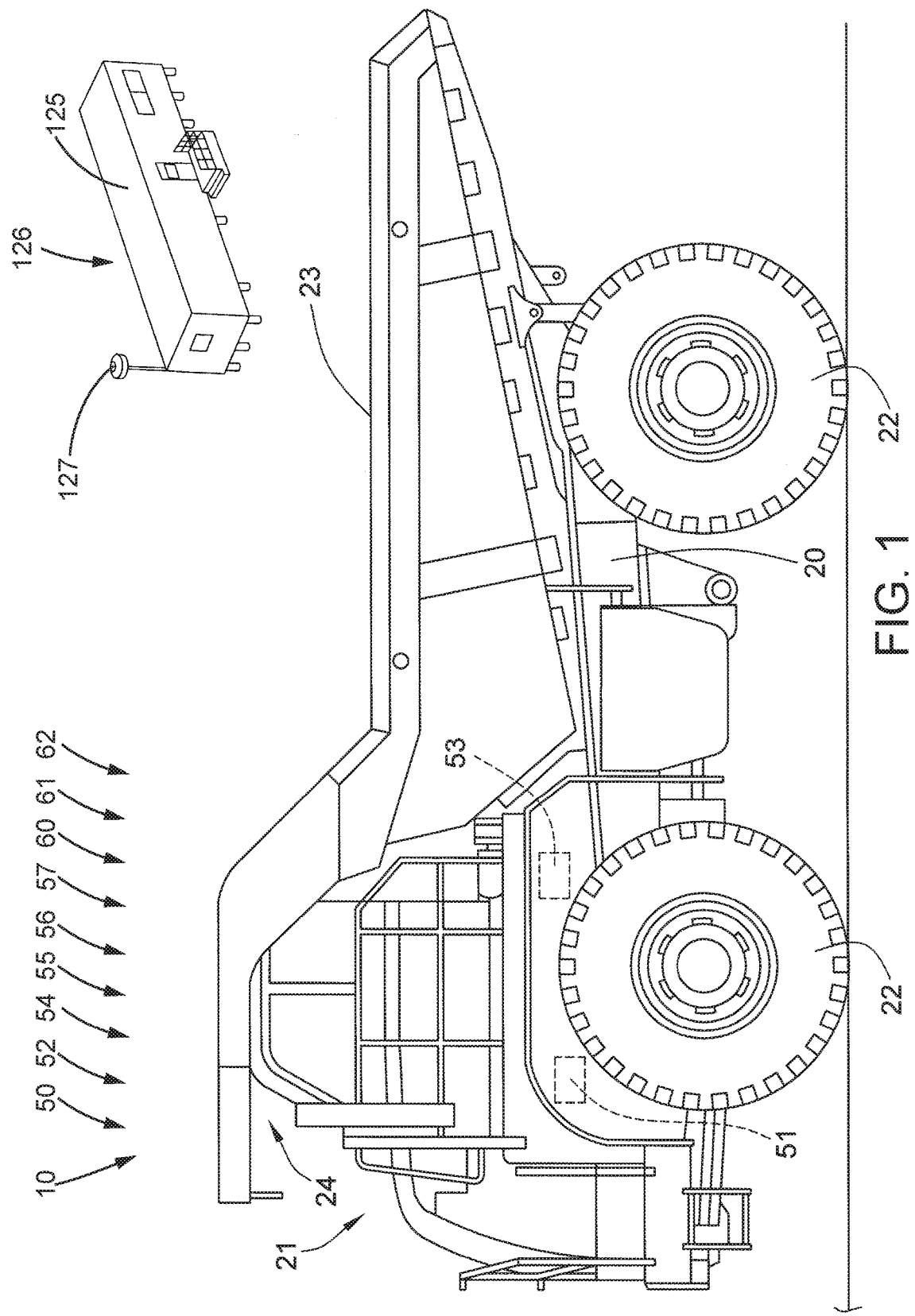
FIG. 1 depicts a schematic illustration of an exemplary machine with which the principles disclosed herein may be used.

FIG. 1 depicts a diagrammatic illustration of a machine 10 for hauling or transporting material. The machine 10 includes a frame 20, and a prime mover such as engine 21 may be operatively connected to drive wheels 22 to propel the machine. The machine 10 may use any type of machine propulsion and drivetrain mechanisms including hydrostatic, electric, or a mechanical drive. A payload container 23 may be pivotally mounted on frame 20 and configured to carry material.

Machine 10 may include a cab 24 that an operator may physically occupy and provide input to control the machine. Cab 24 may include one or more input devices (not shown) through which the operator may issue commands to control the propulsion and steering of the machine as well as dump the payload container 23.

Figure 2:
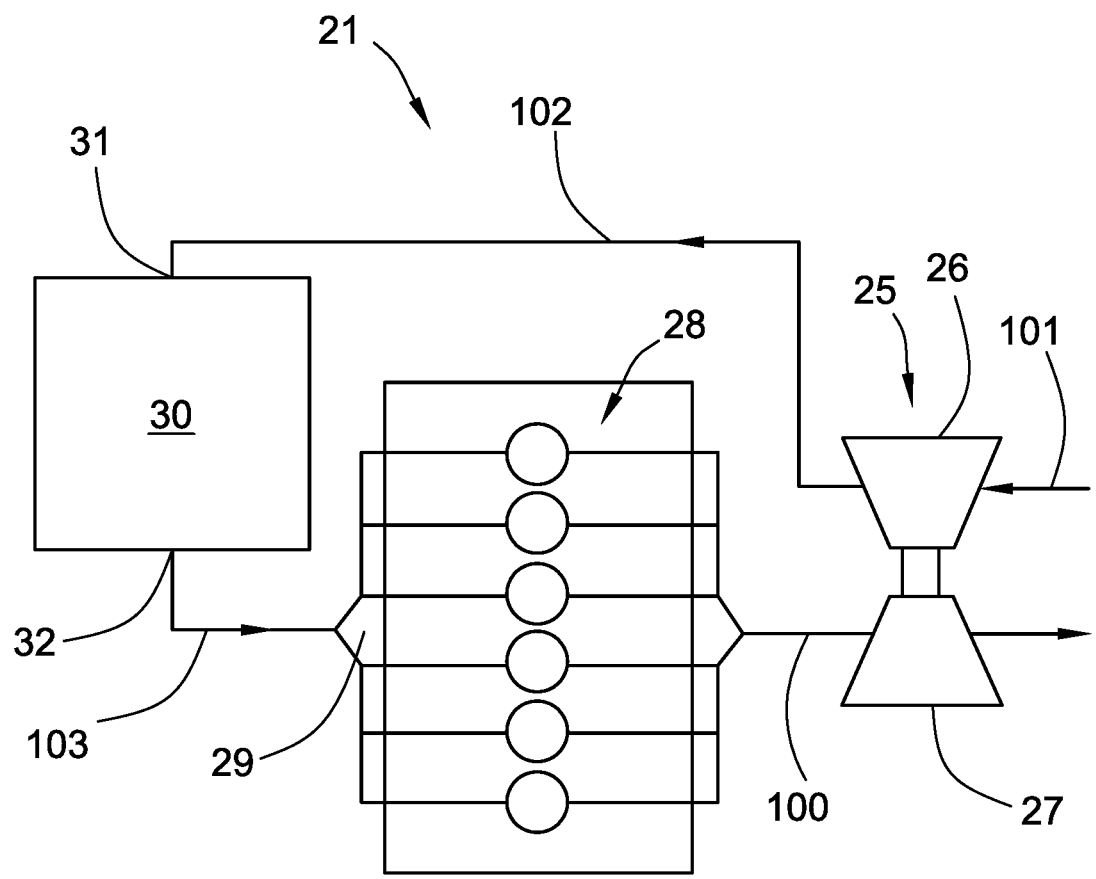
FIG. 2 depicts a schematic illustration of a portion of an engine for use with the machine of FIG. 1.

Referring to FIG. 2, engine 21 may include a turbocharger 25 that includes a turbine 26 and an operatively connected compressor 27. Exhaust gas 100 from engine 21 drives the turbine 26, which causes the compressor 27 to compress intake air 101 to allow a greater mass of fuel/air mixture to enter the cylinders 28 of the engine 21. As a result of the compression, the temperature of the compressed intake air 102 may also increase, which may be undesirable. The compressed intake air 102, sometimes referred to as heated charged air, may be routed through a cooling component 30 such as an air-to-air aftercooler for cooling the heated charged air (the cooled charged air being depicted at 103) prior to it entering the air intake manifold 29 of the engine 21.

Figure 3:
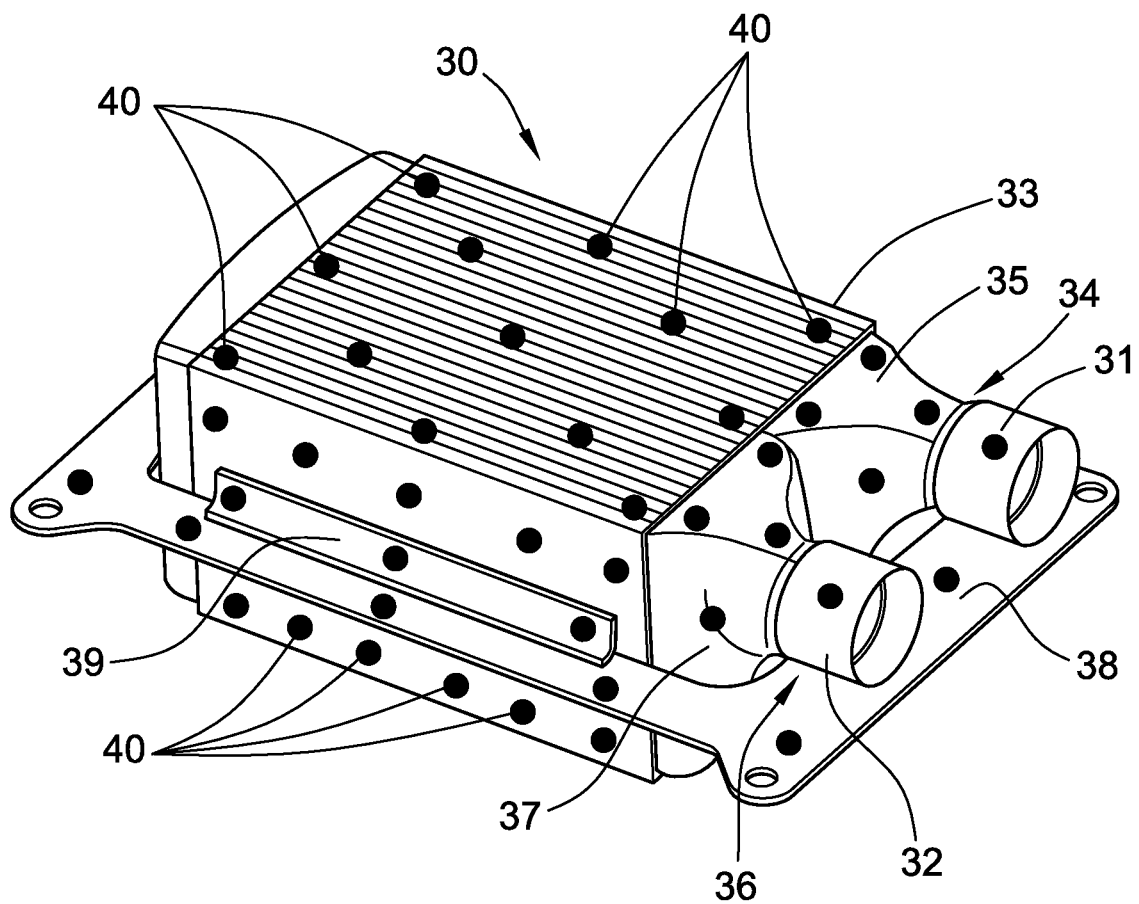
FIG. 3 depicts a perspective view of an aftercooler for use with the engine of FIG. 2.

An exemplary disclosed embodiment of a cooling component 30 is depicted in FIG. 3. Heated charged air may enter the cooling component 30 through an inlet port 31 and be directed into one or more passageways such as tubes (not shown). The heated charged air undergoes a heat exchange operation with respect to relatively cool ambient air as it passes through the passageways and exits through an outlet port 32.

As depicted in FIG. 3, cooling component 30 includes a rectangular heat exchanger section 33 with a plurality of external fins (not shown) operative to exchange heat between air passing through the cooling component and ambient air. Heated charged air enters the cooling component 30 through inlet manifold 34. Inlet manifold 34 may have any configuration but is depicted in FIG. 3 as having a funnel-shaped section 35 fluidly connected to cylindrical inlet port 31. The inlet manifold 34 may be fluidly connected to a plurality of passageways (not shown) within the cooling component 30 that are operatively connected to the heat exchanger section 33. After passing through the passageways, the cooled air exits the cooling component 30 through outlet manifold 36. Outlet manifold 36 may have any configuration but is depicted in FIG. 3 as being generally identical to inlet manifold 34 with a funnel-shaped section 37 fluidly connected to cylindrical outlet port 32.

Cooler component 30 may include a mounting plate 38 for mounting the cooling component on or adjacent the engine 21. One or more mounting brackets 39 may secure or operatively connect the heat exchanger section 33 to the mounting plate 38. In one embodiment, the mounting brackets 39 may be welded to the heat exchanger section 33 and the mounting plate 38.

Other configurations and types of cooling components 30 and other manners of assembling elements or individual parts of the cooling components are contemplated.

Machine 10 may be controlled by a control system 50 as shown generally by an arrow in FIG. 1 indicating association with the machine. The control system 50 may include an electronic control module or controller 51 and a plurality of sensors. The controller 51 may receive input signals from an operator. The controller 51 may control the operation of various aspects of the machine 10 including the drivetrain and the hydraulic systems.

The controller 51 may be an electronic controller that operates in a logical fashion to perform operations, execute control algorithms, store and retrieve data and other desired operations. The controller 51 may include or access memory, secondary storage devices, processors, and any other components for running an application. The memory and secondary storage devices may be in the form of read-only memory (ROM) or random access memory (RAM) or integrated circuitry that is accessible by the controller. Various other circuits may be associated with the controller 51 such as power supply circuitry, signal conditioning circuitry, driver circuitry, and other types of circuitry.

The controller 51 may be a single controller or may include more than one controller disposed to control various functions and/or features of the machine 10. The term "controller" is meant to be used in its broadest sense to include one or more controllers and/or microprocessors that may be associated with the machine 10 and that may cooperate in controlling various functions and operations of the machine. The functionality of the controller 51 may be implemented in hardware and/or software without regard to the functionality. The controller 51 may rely on one or more data maps relating to the operating conditions and the operating environment of the machine 10 that may be stored in the memory of or associated with the controller. Each of these data maps may include a collection of data in the form of tables, graphs, and/or equations.

The control system 50 and controller 51 may be located on the machine 10 as an on-board control system 52, as shown generally by an arrow in FIG. 1 indicating association with the machine, with an on-board controller 53, or may be distributed with components such as an off-board controller 126 also located remotely from or off-board the machine such as at a command center 125 (FIG. 1) located on-site or off-site. The functionality of control system 50 may be distributed so that certain functions are performed at machine 10 and other functions are performed remotely.

Each of machine 10 and the command center 125 may utilize a wireless communications system 127 to permit wireless transmission of information between the machine 10 and the command center 125.

Machine 10 may be equipped with a plurality of machine sensors, as shown generally by arrows in FIG. 1 indicating association with the machine, that provide data indicative (directly or indirectly) of various operating parameters of the machine and/or the operating environment in which the machine is operating. The term "sensor" is meant to be used in its broadest sense to include one or more sensors and related components that may be associated with the machine 10 and that may cooperate to sense various functions, operations, and operating characteristics of the machine and/or aspects of the environment in which the machine is operating. The controller 51 may communicate with the sensors and other components via wired communication lines (not shown) or wirelessly.

Examples of the sensors may include a plurality of sensors associated with the engine 21. For example, a fuel usage sensor 55 may be provided to sense and indicate the amount of fuel being used by the engine 21. A prime mover speed sensor 56 may be provided to sense and indicate the speed of the engine 21. In some instances, the combination of the fuel usage sensor 55 and the prime mover speed sensor 56 may act as the equivalent of a power output sensor. Other manners of determining power output are contemplated. For example, a torque converter speed sensor 57 may be provided and a difference between engine speed and torque converter speed may be indicative of power output. Some or all of the sensors associated with the engine 21 may operate individually or in any combination as a power output sensor for the engine.

Other sensors may be provided that are associated with other aspects of engine 21 or the cooling component 30. For example, an EGR valve position sensor 60 may be provided to sense and indicate the position of the EGR valve on EGR systems (not shown). In some applications, a temperature sensor 61 may be provided to sense and indicate the ambient air temperature. Further, in some applications such as when the cooling component embodies an aftercooler, a fan speed sensor 62 may be provided to sense and indicate the speed of a fan (not shown) associated with the aftercooler.

In each instance, the sensor may generate signals indicative of the relevant function, operation, or characteristic. It should be noted that, in some instances, a temperature sensor may not be required at or adjacent the cooling component 30.

During operation, the cooling component 30 will be exposed to thermal stresses while performing it cooling function. Each cooling component 30 has a useful life that may be dependent upon the thermal stresses to which it has been exposed. The cooling components 30 may fail and require replacement and/or repair as a result of an accumulation of thermal stresses. Control system 50 includes a useful life prediction system 54, as shown generally by an arrow in FIG. 1 indicating association with the machine, that monitors the operation of the machine 10 and, based upon the power output or operation of the engine 21, performs a thermal strain analysis to determine a remaining useful life of the cooling component 30 associated with the machine 10. In some instances, the useful life prediction system 54 may further provide notification of such remaining useful life to desired personnel or systems.

Figure 4:
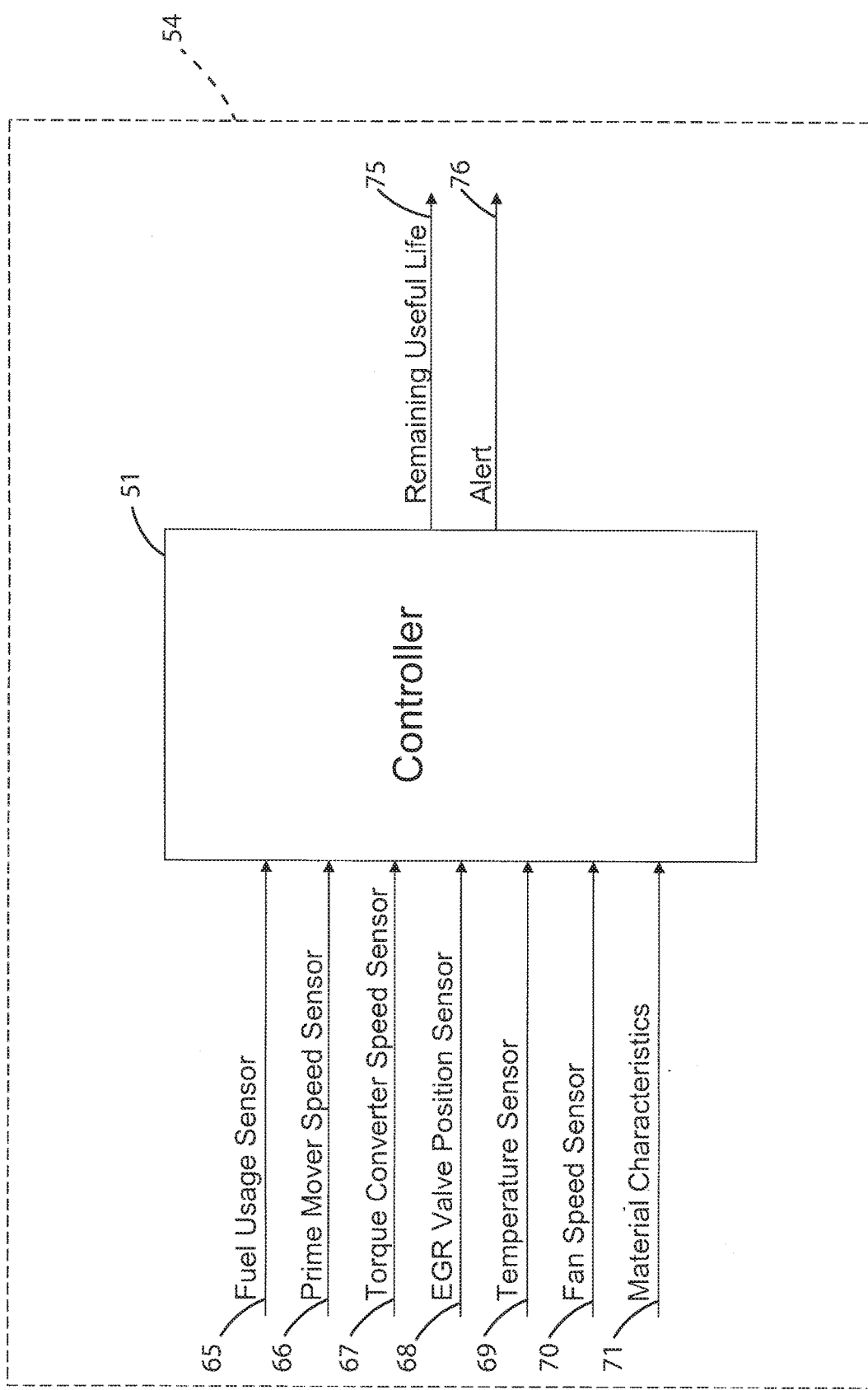
FIG. 4 depicts a block diagram of a useful life prediction system in accordance with the disclosure; and schematic illustration of an idler including an insert with an ID tag exploded therefrom.

As depicted in FIG. 4, the useful life prediction system 54 may be configured so that the controller 51 receives information from various sensors and systems of the machine 10 and processes the information to generate the necessary or desired estimate. As such, all possible inputs are depicted in FIG. 4 even though the useful life prediction system 54 may not use data from all inputs in each instance of operation.

At node 65, the controller 51 may receive fuel usage signals or data from fuel usage sensor 55 (FIG. 2) indicative of the amount of fuel being used by the engine 21. At node 66, the controller 51 may receive engine speed signals or data from prime mover speed sensor 56 indicative of the speed of the engine 21. The controller 51 may use the amount of fuel being used by the engine 21 together with the engine speed to determine the output torque or other measures of power output from the engine. Such determination may be made through the use of empirical data, calculated or theoretical data, or the combination thereof. For example, the analysis may use look-up tables, data maps, equations, or other aspects of the controller 51.

The combination of the fuel usage sensor 55 and the prime mover speed sensor 56 may act as an equivalent of a power output sensor for generating signals indicative of a power output of the engine 21. Other manners of determining the power output of the engine 21 are contemplated. For example, in drive systems having a torque converter, at node 67, the controller 51 may receive torque converter speed signals or data from torque converter speed sensor 57 indicative of the speed of the torque converter. Power output of the engine 21 may be determined by comparing the engine speed based upon signals from the prime mover speed sensor 56 to the torque converter speed based upon signals from the torque converter speed sensor 57.

At node 68, for an engine 21 operatively connected to an EGR system, the controller 51 may receive valve position signals or data from an EGR valve position sensor 60 indicative of the position of the EGR valve. In some systems, the useful life prediction system 54 may use the position of the EGR valve as additional input to determine the power output of the engine 21. When the cooling component 30 is an EGR cooler (not shown), the useful life prediction system 54 may use the position of the EGR valve as additional input to determine the heating characteristics within the EGR cooler.

At node 69, for an engine operatively connected to an aftercooler, the controller 51 may receive temperature signals or data from the temperature sensor 61 indicative of the ambient temperature at the location of the temperature sensor. At node 70, for an engine operatively connected to an aftercooler, the controller 51 may receive fan speed signals or data from the fan speed sensor 62 indicative of the speed of a fan (not shown) associated with the aftercooler. At node 71, the characteristics of the material from which the cooling component 30 is formed may be stored within or by the controller 51. The characteristics may include the maximum accumulated damage permitted for the cooling component 30 or each element of the cooling component.

Controller 51 may generate an estimate of the remaining useful life of the cooling component based upon power output from the engine 21 and other inputs. Accordingly, at node 75, the controller 51 may generate signals that are an estimate of the remaining useful life of the cooling component 30. As the machine 10 operates, the controller 51 may generate at node 76 alerts to inform personnel or other systems of the amount of remaining useful life.

INDUSTRIAL APPLICABILITY

The industrial applicability of the useful life prediction system 54 described herein will be readily appreciated from the forgoing discussion. The foregoing system is applicable to machines 10 having prime movers, such as engines 21, and cooling components 30 that are operated to perform various operations. Such useful life prediction system 54 may be used in any industry and at any operational site in which machine operation is desired.

As machines 10 are operated, cooling components 30, such as aftercoolers, EGR coolers, oil coolers, and other components, will undergo thermal stress due to differences in temperature along the cooling component. Failure of cooling components 30 often results in significant machine downtime, which may result in decreased efficiency and/or increased costs. The useful life prediction system 54 is operative to predict the remaining useful life of cooling components and provide notifications or alerts to personnel or systems. The notifications may be used, for example, as part of a preventative maintenance program to reduce the likelihood of unexpected downtime.

The useful life prediction system 54 may operate by using data from one or more sensors associated with the engine 21 to determine the power output history of the engine of a specified period of time and correlate the power output history to an estimate of the remaining useful life of the cooling component.

Figure 5:
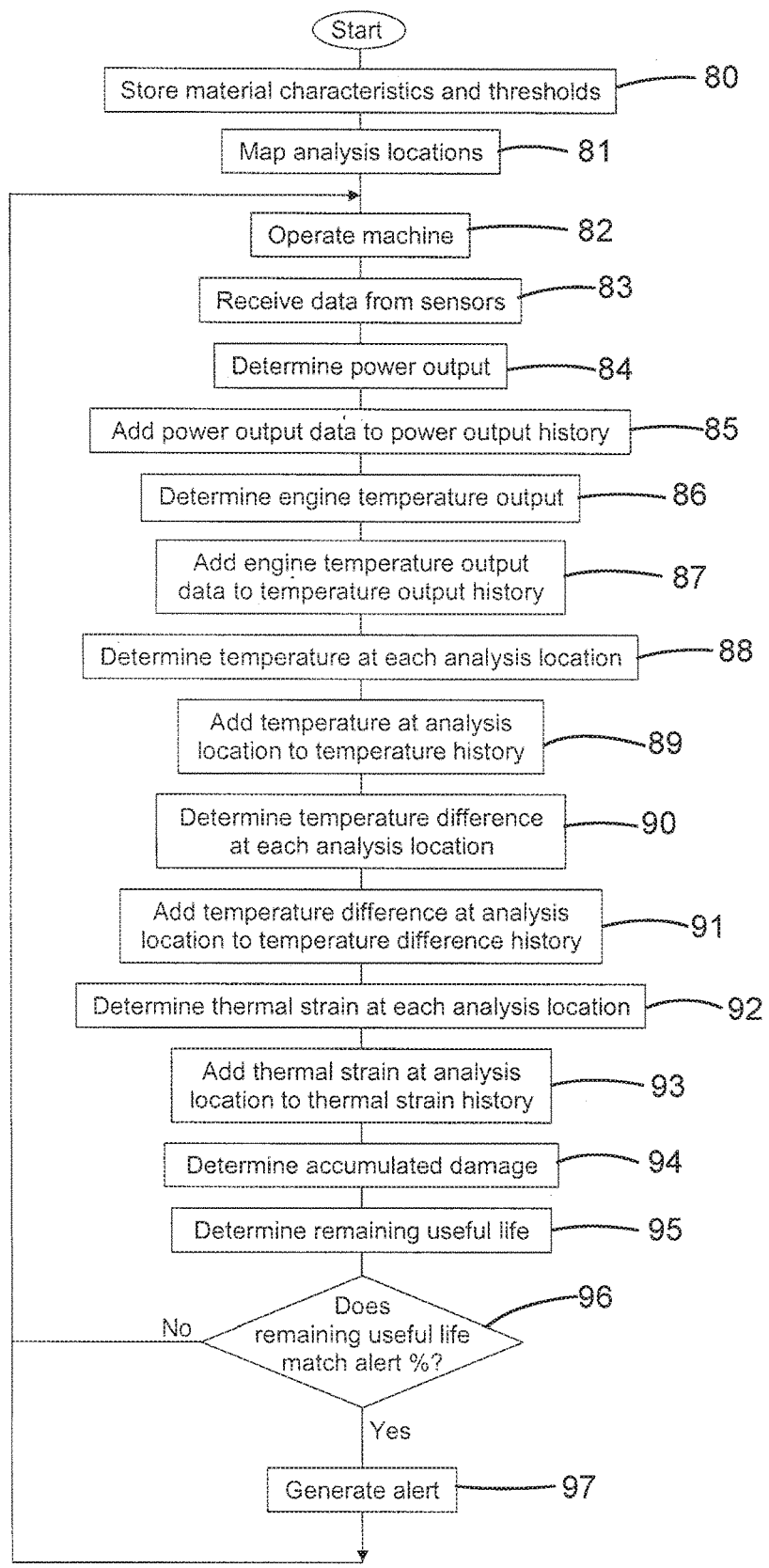
FIG. 5 depicts a flowchart illustrating operation of the useful life prediction system.

FIG. 5 depicts a flowchart of one manner of operation of the useful life prediction system 54. At stage 80, material characteristics of the material from which the cooling component 30 or elements thereof are formed may be set or stored within or by controller 51. The material characteristics may specify the useful life of the cooling component 30. The useful life may be based upon or specified in terms of the estimated amount of accumulated strain that will result in failure of the material. More than one useful life may be utilized if the cooling component 30 is formed from more than one material.

Alert thresholds corresponding to a percentage of useful life of the cooling component 30 may be set for subsequent use to notify personnel or systems of the remaining useful life in order to identify service, inspection and/or replacement intervals for the cooling component 30. In one example, the useful life prediction system 54 may provide a notice in the form of an alert command upon the remaining useful life reaching 50%, 75%, 90%, 95%, and 100%. The useful life prediction system 54 may also provide notices if the cooling component 30 has exceeded its useful life. In some instances, the notice may be provided to a system remote from the machine 10 that includes the engine 21 and cooling component 30.

A plurality of spaced apart locations on the cooling component 30 may be identified or mapped at stage 81 corresponding to or defining a plurality of analysis locations at which temperature analyses may be performed. For example, one or more analysis locations depicted at 40 in FIG. 3 may be located on inlet manifold 34, outlet manifold 35 and at various locations on heat exchanger section 33. Additional analysis locations 40 may also be located on mounting plate 38, mounting brackets 39, and the passageways (not shown) within heat exchanger section 33.

At stage 82, the machine 10 may be operated to perform a function or operation such as material movement, power generation, transportation of objects or people, etc. While operating, the useful life prediction system 54 may perform a thermal strain analysis. For example, the controller may, at stage 83, receive data from the various sensors. More specifically, the controller 51 may receive and store data from one or more of the sensors associated with the engine 21 such as the fuel usage sensor 55, the prime mover speed sensor 56, and the torque converter speed sensor 57. In addition, the controller 51 may receive and store data from the EGR valve position sensor 60, the temperature sensor 61, and the fan speed sensor 62.

At stage 84, the controller may use data from the sensors associated with the engine 21 to determine the power output from the engine. In other words, the controller 51 may determine at desired time intervals the amount of power or power output being generated by the engine 21 based upon one or more outputs from the sensors associated with the engine. The power output at each time interval may be determined by the controller 51 through the use of empirical data, calculated or theoretical data, or the combination thereof. For example, the analysis may use look-up tables, data maps, equations, or in any other manner.

In one embodiment, the controller 51 may determine the power output between 1-5 times per second. The controller 51 may store or record at stage 85 the power output of the engine 21 generated at each time interval or period to define a power output history of the engine. The power output history may include the power output over any desired period of time. In some applications, the power output history may include the entire history of operation since the time the cooling component 30 was placed in operation. In other words, the predetermined period of time that defines the power output history may begin upon the initial operation of the cooling component 30 in connection with the engine 21. In other instances, the power output history may be a shorter time period or analysis window to define a standard or approximation of a power output history that may be applied to a greater period of time.

Based upon the power output at each time interval, the controller 51 may determine at stage 86 a temperature output of the engine 21 for each time interval. For example, based upon the amount of power output of the engine 21, the temperature of various fluids exiting from the engine may be determined. These fluids may include the exhaust gas 100, the oil of the engine 21, coolant for the engine, and any other fluids. The temperature output at each time interval may be determined by the controller 51 through the use of empirical data, calculated or theoretical data, or the combination thereof. For example, the analysis may use look-up tables, data maps, equations, or in any other manner. The controller 51 may store or record at stage 87 the temperature output of the engine 21 at each time interval over the desired time period corresponding to the power output history to define a temperature output history.

The controller 51 may utilize the temperature output at each time interval to determine at stage 88 a temperature at each analysis location 40. The temperature at each analysis location 40 for each time interval may be determined by the controller 51 through the use of empirical data, calculated or theoretical data, or the combination thereof. For example, the analysis may use look-up tables, data maps, equations, or in any other manner. In one example, the temperature at each analysis location 40 may be determined through the use of heat transfer equations based upon the materials from which the cooling component 30 is formed, characteristics of the assembly, and the environmental conditions. The controller 51 may store or record at stage 89 the temperature at each analysis location 40 at each time interval over the desired time period corresponding to the power output history to define a temperature history at each of the analysis locations.

The controller 51 may utilize the temperature at each analysis location 40 at each time interval to determine at stage 90 a temperature difference between each analysis location. The temperature difference at each analysis location 40 relative to each of the other analysis locations for each time interval may be determined by the controller 51 in any desired manner. The controller 51 may store or record at stage 91 the temperature difference at each analysis location 40 relative to each of the other analysis locations at each time interval over the desired time period corresponding to the power output history to define a temperature difference history for each of the analysis locations.

The temperature difference at each analysis location 40 relative to each of the other analysis locations for each time interval may be used by the controller 51 to determine at stage 92 the thermal strain at each analysis location 40 as a result of the temperature differences. The thermal strain at each analysis location 40 and for each time interval may be determined by the controller 51 through the use of empirical data, calculated or theoretical data, or the combination thereof. For example, the analysis may use look-up tables, data maps, equations, or in any other manner. The controller 51 may select the maximum thermal strain at specified analysis locations 40 or may otherwise prioritize or weigh the selection of thermal strain values for each location and each time interval. The controller 51 may store or record at stage 93 the maximum thermal strain at each analysis location 40 at each time interval over the desired time period corresponding to the power output history to define a thermal strain history for each of the analysis locations.

The controller 51 may measure or determine at stage 94 the accumulated damage to the cooling component 30 at each analysis location 40 based upon the maximum or selected thermal strain at each analysis location 40 at each time interval. Such measurement may be performed in any desired manner. In one embodiment, the controller 51 may utilize a rainflow analysis or counting process. The analysis may be performed in an ongoing manner upon completion or during at each time interval or the analysis may be performed after a predetermined period of time using the thermal strain history for that period of time.

At stage 95, the controller 51 may compare the accumulated damage to the material characteristics of the material from which the cooling component 30 is formed to determine the remaining useful life of the cooling component. The controller 51 may at stage 96 compare the remaining useful life of the cooling component 30 to the alert threshold to determine whether an alert or notice of the remaining useful life should be sent to specified personnel or another system. If the remaining useful life matches one of the alert percentages, the controller 51 may generate an alert command at stage 97 and stages 82-96 repeated. If the remaining useful life does not match one of the alert percentages, an alert command is not generated and stages 82-96 repeated.

Various alternate embodiments or alternate manners of operation are contemplated. For example, as stated above, the power output from the engine 21 may be determined in any desired manner based upon signals from one or more sensors associated with the engine.

In addition, in some instances, the controller 51 may not determine a temperature difference between every analysis location 40 but rather may determine a temperature difference between each analysis location and only some of the other analysis locations. In other words, the controller 51 may prioritize the temperature differences in order to prioritize the thermal strain at selected ones of the analysis locations. Temperature differences that are expected to have minimal impact on the life of the cooling component 30 may not be analyzed in order to simplify the analysis. In other instances, temperature differences between selected analysis locations may be prioritized or given greater weight during the analysis process. In still other instances, it may be possible for the controller 51 to determine a temperature difference between each analysis location 40 and a selected one of the other analysis locations. In a further example, temperature differences may be determined between each analysis location 40 and another location at which the temperature is determined but a thermal strain analysis is not performed.

In some instances, the analyses may be performed by the controller 51 based upon empirical data which may be stored within look-up tables or data maps of the controller. In other instances, the analyses may be performed by the controller 51 based upon equations that are either stored within the controller or the solutions to which are stored within look-up tables or data maps of the controller. In still other instances, the analyses may be performed by a combination of processes.

The flowchart of FIG. 5 describes the useful life prediction system 54 as generating each data set (e.g., power output, engine temperature output, temperature at each analysis location 40, temperature difference or gradient, maximum thermal strain) for each time interval until determining an amount of damage for that time interval and then adding the damages to determine an accumulated damage and the remaining useful life. However, the useful life prediction system 54 may also determine a first history and then using that history to generate subsequent histories until the remaining useful life is determined. In other words, the power output history may be stored or generated and the useful life prediction system 54 may operate to periodically use the power output history to determine the other histories (e.g., temperature output history, temperature history at each analysis location 40, temperature difference history at each analysis location, thermal strain history) to determine the remaining useful life of the cooling component 30.

Still further, the controller 51 may be configured to use either process but only over a relatively short period of time or window and then utilize the accumulated damage over that relatively short window to generate a standard accumulated damage for a specified time period. More specifically, if actual power output data is not available for the entire time the cooling component 30 has been in service, an estimate of the accumulated damage may be determined by determining or generating a standard amount of accumulated damage per a specified number of hours of operation and estimating the number of hours that the cooling component has been in operation.

It will be appreciated that the foregoing description provides examples of the disclosed system and technique. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

The invention claimed is:

1. A system for determining a remaining useful life of a cooling component operatively connected to a prime mover, comprising:
    a power output sensor associated with the prime mover and configured to generate sensor signals indicative of a power output of the prime mover; and
    a controller configured to:
        store material characteristics of the cooling component;
        store a plurality of spaced apart locations of the cooling component that define a plurality of analysis locations;
        perform a thermal strain analysis including:
            receiving sensor signals from the power output sensor;
            determining the power output of the prime mover based upon the sensor signals;
            determining a temperature output of the prime mover based upon the power output;
            determining a temperature at each of the plurality of analysis locations based upon the temperature output;
            determining a temperature difference between at least some of the plurality of analysis locations and another of the plurality of analysis locations based upon the temperature at each respective one of the plurality of analysis locations; and
            determining a thermal strain for each of the at least some of the plurality of analysis locations based upon the temperature difference;
        repeat the thermal strain analysis at predetermined time intervals over a predetermined period of time;
        determine an accumulated damage for the cooling component based upon the thermal strain from each thermal strain analysis; and
        determine a remaining useful life of the cooling component based upon the material characteristics and the accumulated damage.

2. The system of claim 1, wherein the thermal strain analysis further includes determining a temperature difference between at least some of the plurality of analysis locations and others of the plurality of analysis locations based upon the temperature at each respective one of the plurality of analysis locations.

3. The system of claim 1, wherein the thermal strain analysis further includes determining a temperature difference between each of the plurality of analysis locations and others of the plurality of analysis locations based upon the temperature at each respective one of the plurality of analysis locations.

4. The system of claim 1, wherein the thermal strain analysis over the predetermined period of time defines a thermal strain history and the accumulated damage is determined based upon the thermal strain history.

5. The system of claim 4, wherein the accumulated damage is determined after determining the thermal strain history.

6. The system of claim 1, wherein the accumulated damage is determined upon determining the thermal strain at each predetermined time interval.

7. The system of claim 1, wherein the accumulated damage is determined using a rainflow analysis.

8. The system of claim 1, wherein the predetermined period of time begins upon initial operation of the cooling component in connection with the prime mover.

9. The system of claim 1, wherein the predetermined period of time defines an analysis window and further including determining an accumulated damage per unit time based upon the analysis window and determining each power output of the prime mover while operatively connected to the cooling component to define a power output history, and the accumulated damage is determined based upon the accumulated damage per unit time and the power output history.

10. The system of claim 1, wherein the controller is further configured to store an alert threshold corresponding to a percentage of useful life of the cooling component and generate an alert command if the remaining useful life equals the alert threshold.

11. The system of claim 10, wherein the alert command is communicated to a system remote from a machine comprising the prime mover.

12. The system of claim 1, wherein the controller is further configured to:
    determine a power output history based upon the power output over the predetermined period of time;
    determine a temperature output history based upon the power output history;
    determine a temperature history at each of the plurality of analysis locations based upon the temperature output history;
    determine a temperature difference history between at least some of the plurality of analysis locations and another of the plurality of analysis locations based upon the temperature at each respective one of the plurality of analysis locations;
    determine a thermal strain history for each of the at least some of the plurality of analysis locations based upon the temperature difference history; and
    determine the accumulated damage for the cooling component based upon the thermal strain history.

13. The system of claim 1, wherein the power output sensor comprises a fuel usage sensor associated with the prime mover and configured to generate fuel usage signals indicative of a fuel usage of the prime mover and a prime mover speed sensor associated with the prime mover and configured to generate speed signals indicative of a prime mover speed of the prime mover, and the controller is configured to receive the fuel usage signals, determine the fuel usage based upon the fuel usage signals, receive the speed signals, determine the prime mover speed based upon the speed signals, and determine the power output based upon the fuel usage and the prime mover speed.

14. A controller-implemented method for determining a remaining useful life of a cooling component operatively connected to a prime mover, comprising:
storing material characteristics of the cooling component;
storing a plurality of spaced apart locations of the cooling component that define a plurality of analysis locations;
performing a thermal strain analysis including:
receiving sensor signals from a power output sensor indicative of a power output of the prime mover;
determining the power output of the prime mover based upon the sensor signals;
determining a temperature output of the prime mover based upon the power output;
determining a temperature at each of the plurality of analysis locations based upon the temperature output;
determining a temperature difference between at least some of the plurality of analysis locations and another of the plurality of analysis locations based upon the temperature at each respective one of the plurality of analysis locations; and
determining a thermal strain for each of the at least some of the plurality of analysis locations based upon the temperature difference;
repeating the thermal strain analysis at predetermined time intervals over a predetermined period of time;
determining an accumulated damage for the cooling component based upon the thermal strain from each thermal strain analysis; and
determining a remaining useful life of the cooling component based upon the material characteristics and the accumulated damage.

15. The method of claim 14, wherein the thermal strain analysis further includes determining a temperature difference between at least some of the plurality of analysis locations and others of the plurality of analysis locations based upon the temperature at each respective one of the plurality of analysis locations.

16. The method of claim 14, wherein the thermal strain analysis further includes determining a temperature difference between each of the plurality of analysis locations and others of the plurality of analysis locations based upon the temperature at each respective one of the plurality of analysis locations.

17. The method of claim 14, wherein the thermal strain analysis over the predetermined period of time defines a thermal strain history and further including determining the accumulated damage based upon the thermal strain history.

18. The method of claim 17, further including determining the accumulated damage after determining the thermal strain history.

19. The method of claim 14, further including determining the accumulated damage upon determining the thermal strain at each predetermined time interval.

20. A machine, comprising:
a prime mover;
a cooling component operatively connected to the prime mover;
a power output sensor associated with the prime mover and configured to generate sensor signals indicative of a power output of the prime mover; and
a controller configured to:
store material characteristics of the cooling component;
store a plurality of spaced apart locations of the cooling component that define a plurality of analysis locations;
perform a thermal strain analysis including:
receiving sensor signals from the power output sensor;
determining the power output of the prime mover based upon the sensor signals;
determining a temperature output of the prime mover based upon the power output;
determining a temperature at each of the plurality of analysis locations based upon the temperature output;
determining a temperature difference between at least some of the plurality of analysis locations and another of the plurality of analysis locations based upon the temperature at each respective one of the plurality of analysis locations; and
determining a thermal strain for each of the at least some of the plurality of analysis locations based upon the temperature difference;
repeat the thermal strain analysis at predetermined time intervals over a predetermined period of time;
determine an accumulated damage for the cooling component based upon the thermal strain from each thermal strain analysis; and
determine a remaining useful life of the cooling component based upon the material characteristics and the accumulated damage.

* * * * *